(12) United States Patent  
Tanaka

(10) Patent No.: US 7,927,300 B2  
(45) Date of Patent: Apr. 19, 2011

(54) ULTRASONIC OPERATION APPARATUS FOR DETECTING INITIAL RESONANCE FREQUENCY AND FOR SHIFTING TO PLL OPERATION

(75) Inventor: Kazue Tanaka, Tokyo (JP)

(73) Assignee: Olympus Corporation, Tokyo (JP)

( * ) Notice: Subject to any disclaimer, the term of this patent is extended or adjusted under 35 U.S.C. 154(b) by 490 days.

(21) Appl. No.: 12/125,461

(22) Filed: May 22, 2008

(65) Prior Publication Data

US 2008/0234712 A1  Sep. 25, 2008

Related U.S. Application Data

(62) Division of application No. 10/706,642, filed on Nov. 12, 2003, now Pat. No. 7,393,356.

(30) Foreign Application Priority Data

Nov. 22, 2002  (JP) ................................. 2002-339715  
Jul. 23, 2003  (JP) ................................. 2003-200808

(51) Int. Cl.  
A61B 17/00  (2006.01)

(52) U.S. Cl. ............................... 604/22; 601/2; 606/167

(58) Field of Classification Search .................. 600/459; 601/2–4; 606/167–171; 604/22  
See application file for complete search history.

(56) References Cited

U.S. PATENT DOCUMENTS 6,678,621 B2   1/2004  Wiener et al.

FOREIGN PATENT DOCUMENTS

JP  2002-45368  2/2002  
JP  2002-177292  6/2002

*Primary Examiner* — Brian Casler  
*Assistant Examiner* — Parikha S Mehta  
(74) *Attorney, Agent, or Firm* — Scully, Scott, Murphy & Presser, P.C.

(57) ABSTRACT

In an ultrasonic operation apparatus according to the present invention, in order to detect the initial resonance frequency (Fro) promptly once a foot switch is pressed, under the control of a sweeping speed control circuit, the D/A converter D/A converts 8-bits of signals (phase difference amount signal $\Delta\theta$) representing the amount of the phase difference detected by the phase comparator, and the output of the D/A converter is output to a VCO so as to become a clock for a sweep circuit. When a phase difference amount between $\theta i$ and $\theta v$ is large and a drive frequency setting signal (Fs) is far from Fro, the sweeping speed for Fro detection is increased. When a phase difference amount between $\theta i$ and $\theta v$ is small and Fs is close to Fro, the sweeping speed for Pro detection is decreased.

16 Claims, 12 Drawing Sheets

ULTRASONIC OPERATION APPARATUS FOR DETECTING INITIAL RESONANCE FREQUENCY AND FOR SHIFTING TO PLL OPERATION

This application is a divisional of Ser. No. 10/706,642 U.S. Pat. No. 7,393,356, filed on Nov. 12, 2003 and issued on Jul. 1, 2008, which claims benefit of Japanese Patent No. 4084253 filed in Japan on Jul. 23, 2003 and issued on Feb. 22, 2008, the entire contents of each of which are incorporated herein by their reference.

BACKGROUND OF THE INVENTION

1. Field of the Invention

The present invention relates to an ultrasonic operation apparatus and, in more particular, to an ultrasonic operation apparatus uniquely detecting and controlling resonance frequencies.

2. Description of the Related Art

Conventionally, various kinds of ultrasonic apparatus using ultrasonic vibrators as ultrasonic converters have been proposed, and, for example, a surgical ultrasonic knife and/or an ultrasonic processing apparatus have been known.

An ultrasonic vibrator used in a surgical ultrasonic knife or an ultrasonic processing apparatus has higher conversion efficiency. Therefore, it has been conventionally known that the ultrasonic vibrator is driven at the mechanical resonance point of the ultrasonic vibrator.

The most common unit to be resonated at the mechanical resonance point is a resonance point tracking circuit according to the so-called phase-locked loop (PLL) method. The resonance point tracking circuit detects the phases of voltage to be applied to an ultrasonic vibrator and of the fed current and controls such that the phase difference can be zero.

This is excellent method for tracking the changes in load to be applied to the ultrasonic vibrator since the ultrasonic vibrator can be driven securely at the resonance point.

However, in order to perform resonance-point tracking by using the PLL, an initial resonance frequency (Fro) in accordance with a probe connected to the vibrator must be securely detected, as shown in FIG. 10, before the tracking operation.

An initial resonance frequency (Fro) may depend on the type of probe connected to the vibrator, variation in material and workmanship and/or ambient temperature.

Like the one disclosed in Japanese Unexamined Patent Application Publication No. 2002-45368, in order to detect an initial resonance frequency (Fro), output frequencies are swept. When the initial resonance frequency (Fro) is detected by detecting the current and changes in phase during the sweeping, a PLL method automatic tracking operation at the resonance point, which changes in operation, is performed.

FIG. 11 describes the conventional technology and includes an ultrasonic vibrator 114, an ultrasonic operation apparatus 110, and a foot switch 101. The ultrasonic vibrator 114 has an ultrasonic vibrator 114a and a probe 114b. The ultrasonic vibrator 114 has an initial resonance frequency (Fro). The foot switch 101 controls ultrasonic outputs of the ultrasonic operation apparatus 100.

The ultrasonic operation apparatus 100 includes a CPU 102, a hand-piece (HP) discriminating circuit 110, a PLL control circuit 116, a sweep circuit 103, a resonance frequency detecting circuit 113, a multiplier 105, a power amplifier 109, and a detecting circuit 112. The CPU 102 performs the main control of the ultrasonic operation apparatus 100. The HP discriminating circuit 110 discriminates the type of the connected ultrasonic vibrator. The PLL control circuit 116 performs PLL operations. The sweep circuit 103 sweeps frequencies of ultrasonic outputs when the initial resonance frequency (Fro) is detected. The resonance frequency detecting circuit 113 detects the change from + to − in phase differences between the voltage of the ultrasonic output and current phase signals. The multiplier 105 multiplies a set signal DA1 for setting the magnitude of an ultrasonic output to SIN waveforms to be output from a DDS 107 for generating SIN waveforms. The power amplifier 109 amplifies ultrasonic outputs. The detecting circuit 112 detects the voltage and current signals of ultrasonic outputs.

When an operator turns ON the foot switch 101, 8-bits of initial setting frequency signals (Fo) are sent from the CPU 102 to the sweep circuit 103. Then, a sweep start signal (/SWEEP_ON) is sent, and the sweeping of the output frequencies for detecting the initial resonance frequency (Fro) is started. Here, the initial setting frequency signal (Fo) is a frequency for starting the frequency sweep.

According to the output setting for the detection of the initial resonance frequency (Fro), 4-bits of output current signals are output from the CPU 102 to a D/A converter 104. The output current signals are D/A-converted in the D/A converter 104 and are output to the multiplier 105.

The sweep circuit 103 down-counts the initial setting frequency signals (Fo) at constant time intervals and generates sweep signals (Fo'). When the initial resonance frequency (Fro) is detected, the initial setting frequency signals (Fo) pass through an UP/DOWN counter 106 and become drive frequency setting signals (Fs). Then, the drive frequency setting signals (Fs) are input to the DDS 107.

The UP/DOWN counter 106 functions during the PLL tracking operation and is used for tracking frequencies.

Therefore, the UP/DOWN counter 106 is designed so as to operate only when the input PLL_ON signal is ON. The input PLL_ON signal is turned on when the initial resonance frequency (Fro) is detected.

The DDS 107 outputs SIN waveforms in accordance with the drive frequency setting signal (Fs), and the SIN waveform output from the DDS 107 is input to the multiplier 105. Then, the output current signal from the CPU 102 is multiplied by the signal DA1, which has been D/A-converted in the D/A converter 104.

The SIN waveforms output from the multiplier 105 are amplified in the power amplifier 109 and are output to the ultrasonic vibrator 114a through the detecting circuit 112. Then, the probe 114b connected to the ultrasonic vibrator 114a is ultrasonically vibrated.

In the detecting circuit 112, the phase signals θv (voltage phase signal) and θi (current phase signal) of the ultrasonic outputs (voltage and current) are detected and are output to a phase comparator 108 and the resonance frequency detecting circuit 113. Furthermore, the effective value |I| of the output current is detected and is output to the CPU 102 through an A/D converter 111.

The CPU 102 monitors the effective value |I| of the output current from the frequency sweeping when the initial resonance frequency (Fro) is detected. If the effective value |I| exceeds a predetermined threshold value |I|ref, the enable signal /PHA_EN is turned on for the resonance frequency detecting circuit 113. Then, the operation of the resonance frequency detecting circuit 113 is started.

The resonance frequency detecting circuit 113 detects the phase difference between the voltage phase signal θv and the current phase signal θi and detects the frequency where the phase difference changes from + to − (that is, where the phase difference is zero) as the initial resonance frequency (Fro). Then, the PLL_ON is turned on. If the initial resonance frequency (Pro) cannot be detected during one sweep of output frequencies, the detection of the initial resonance frequency (Fro) is performed again (twice maximum).

The sweep circuit 103 in which the PLL_ON is turned on stops the frequency sweeping and keeps the frequency changes below the detected resonance frequency.

Because the PLL_ON is turned on, the UP/DOWN counter 106 and the phase comparator 108 start operating, and the PLL 116 performs the tracking of resonance frequency.

The phase comparator 108 detects the phase difference between the voltage phase signal $\theta v$ and the current phase signal $\theta i$. Then, for the frequency tracking, the phase comparator 108 outputs a control signal (called UP/DOWN signal, hereinafter) for raising or lowering the output frequency of the output (SIN waveform) from the DDS 107. Then, the UP/DOWN signal is input to the UP/DOWN counter 106.

The UP/DOWN counter 106 outputs a drive frequency setting signal (Fs) based on the initial resonance frequency (Fro) detected when the resonance frequency is detected and the UP/DOWN signal from the phase comparator 108. The drive frequency setting signal (Fs) is a frequency setting signal to be actually output from the DDS 107.

Next, the processing flow will be described up to the PLL pull-in in a conventional ultrasonic coagulation/resection apparatus having the above-described construction.

As shown in FIG. 12, when an operator turns on the foot switch 101 at a step S101, the CPU 102 outputs 4-bits of output current signals to the D/A converter 104 in order to set the output when the initial resonance frequency (Fro) is detected at a step S102. Then, the D/A converter 104 D/A converts and outputs the 4-bits of output current signals to the multiplier 105.

At a step S103, the CPU 102 sends 8-bits of initial setting frequency signals (Fo) to the sweep circuit 103. Then, a sweep start signal (/SWEEP_ON) is sent, and the sweeping of the output frequencies for detecting the initial resonance frequency (Fro) is started.

At a step S104, the number of sweeps is counted, and it is determined at a step S105 whether the effective value |I| of the output current exceeds the threshold value |I|ref or not. If the effective value |I| of the output current exceeds the threshold value |I|ref, it is determined at a step S106 whether the phase difference between the voltage phase signal $\theta v$ and the current phase signal $\theta i$ changes from + to –. If the change from + to – is detected, the change is detected as the initial resonance frequency (Fro). At a step S107, the frequency sweeping is stopped, and the operations of the UP/DOWN counter 106 and the phase comparator 108 are started. Thus, the tracking of resonance frequencies by the PLL 116 is performed.

If it is determined at the step S105 that the effective value |I| of the output current does not exceed the threshold value |I|ref, it is determined at a step S108 whether the number of sweeps is two or not. If the first sweeping has been performed, the processing returns to the step S103. Then, the subsequent steps are performed. If the second sweeping has been performed, an alarm is given and the output is stopped at a step S109.

SUMMARY OF THE INVENTION

Accordingly, it is an object of the present invention to provide an ultrasonic operation apparatus for detecting an initial resonance frequency (Fro) securely, fast and properly in order to shift to a PLL operation.

According to one aspect of the invention, there is provided an ultrasonic operation apparatus, including a driving signal generating portion for generating a driving signal, which can drive an ultrasonic vibrator for causing ultrasonic vibrations, a frequency control portion for controlling oscillation frequencies of the driving signal generating portion based on the phase information of a driving signal supplied from the driving signal generating portion to the ultrasonic vibrator, a sweep portion for controlling the frequency control portion and for frequency-sweeping the driving signal, and a sweep operation control portion for controlling an operation of the sweep portion based on the characteristic of the ultrasonic vibrator.

The other features and advantages of the present invention will be fully apparent from the descriptions below.

BRIEF DESCRIPTION OF THE DRAWINGS

FIG. 1 is a construction diagram showing a construction of an ultrasonic operation apparatus;

FIG. 2 is a block diagram showing the construction of the ultrasonic operation apparatus in FIG. 1; and FIG. 3 is a block diagram showing a construction of a variation example of the ultrasonic operation apparatus in FIG. 2.

FIG. 4 is a block diagram showing a construction of an ultrasonic operation apparatus; and FIG. 5 is a block diagram showing a construction of a variation example of the ultrasonic operation apparatus in FIG. 4.

FIG. 8 is a block diagram showing a construction of an ultrasonic operation apparatus; and FIG. 9 is a flowchart showing an operation of the ultrasonic operation apparatus in FIG. 8.

FIG. 10 is a diagram describing the detection of a resonance frequency of a conventional ultrasonic coagulation/resection apparatus;

FIG. 11 is a block diagram showing a construction of the conventional ultrasonic coagulation/resection apparatus; and FIG. 12 is a flowchart describing an operation of the ultrasonic coagulation/rejection apparatus in FIG. 11.

DETAILED DESCRIPTION OF THE PREFERRED EMBODIMENTS

First Embodiment

Figure 1:
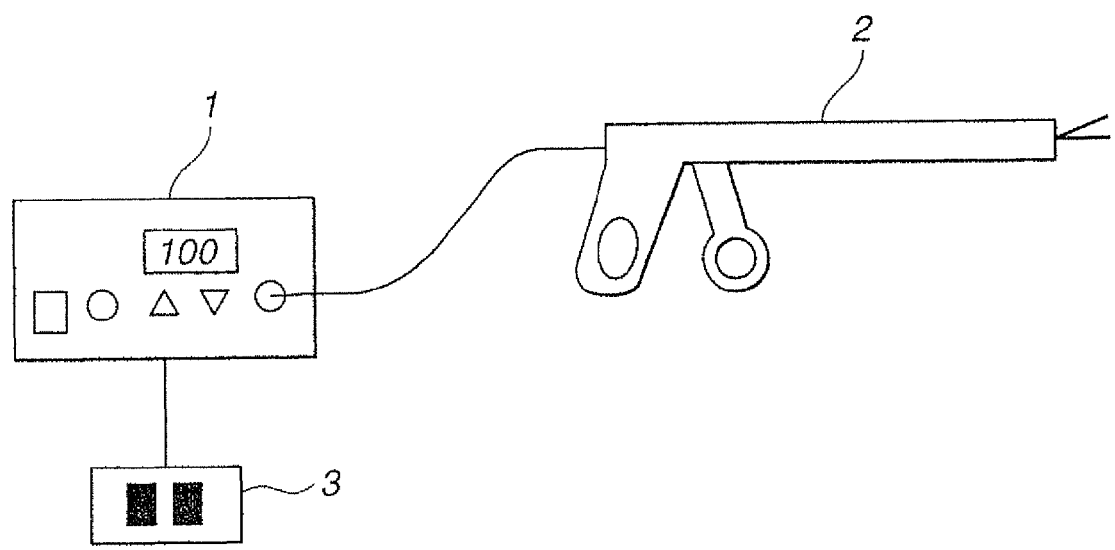
FIGS. 1 to 3 relate to a first embodiment of the present invention.

An ultrasonic operation apparatus according to a first embodiment includes, as shown in FIG. 1, an ultrasonic coagulation/resection apparatus 1, a hand piece 2 and a foot switch 3. The ultrasonic coagulation/resection apparatus 1 outputs ultrasound. The hand piece 2 is used for treating. The foot switch 3 is used for controlling the ultrasonic outputs of the ultrasonic coagulation/resection apparatus 1.

Figure 2:
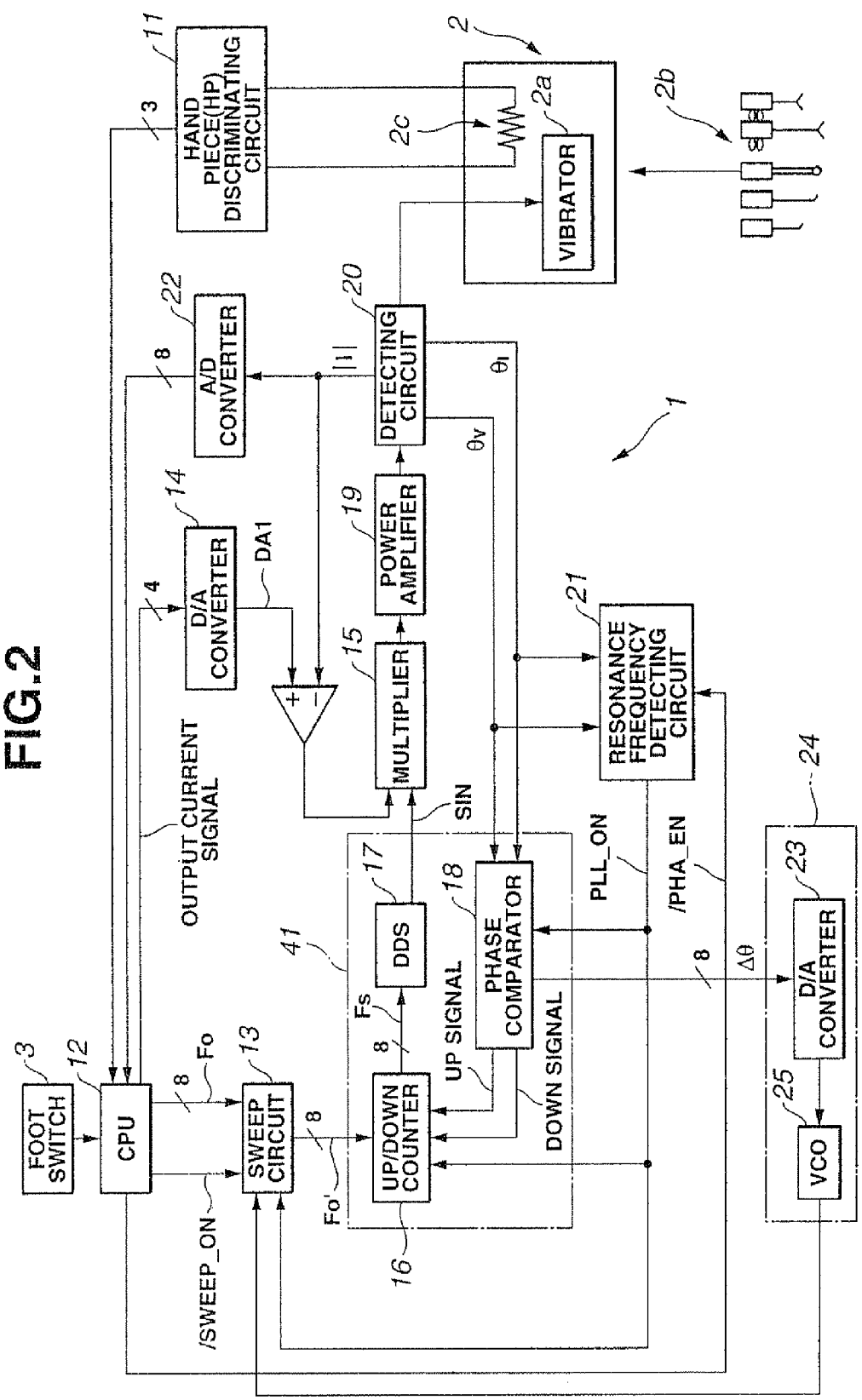

As shown in FIG. 2, the hand piece 2 includes a vibrator 2*a* (the band 20 kHz, 40 kHz or 100 kHz) having a unique frequency band and a probe 2*b*. The probe 2*b* may vary in form. Due to the production variation, the initial resonance frequency (Fro) may vary in the range of several kHz. The hand piece 2 can be removably connected to the ultrasonic coagulation/resection apparatus 1.

Electric signals supplied from the ultrasonic coagulation/resection apparatus 1 are converted to mechanical vibrations in the vibrator 2a, and the treatment is performed with the mechanical vibrations of the probe 2b connected to the vibrator 2a.

The hand piece 2 has a discriminating resistance 2c for discriminating the frequency band of the vibrator 2a, the impedance of the probe 2b connectable to the hand piece 2 and so on. The discriminating resistance 2c has a different constant in accordance with the difference in frequency band (rough frequency band such as 20 kHz, 40 kHz and 100 kHz) of the vibrator 2a, maximum value of the output current and impedance. A hand piece (HP) discriminating circuit 11 detects the resistance value of the discriminating resistance 2c and sends the detected result (frequency band) to the CPU 12. The CPU 12 determines the type of the connected vibrator based on the result.

In the ultrasonic coagulation/resection apparatus 1, when an operator turns on the foot switch 3 as shown in FIG. 2, the CPU 12 sends 8-bits of initial setting frequency signals (Fo) to the sweep circuit 13 in accordance with the discrimination result of the hand piece 2. Then, a sweep signal (/SWEEP_ON) is sent, and the sweep of output frequencies for detecting the initial resonance frequency (Fro) is started.

Here, the initial setting frequency signal (Fo) is a frequency for starting frequency-sweeping. For example, when the frequency band having the initial resonance frequency (Fro) of the hand piece 2 is 20 kHz, the initial setting frequency signal (Fo) corresponding to 30 kHz is sent. When the frequency band of the hand piece 2 is 40 kHz, the initial setting frequency signal (Fo) corresponding to 50 kHz is sent.

According to the ultrasonic output setting for detecting the initial resonance frequency (Fro), the CPU 12 outputs 4-bits of output current signals (30% of the maximum output) to the D/A converter 14. The D/A converter 14 D/A converts and outputs the output current signals to the multiplier 15.

The sweep circuit 13 generates a sweep signal (F0') by down-counting the initial setting frequency signals (Fo) in accordance with the output frequency of a sweeping speed control circuit 26. When the initial resonance frequency (Fro) is detected, the sweep signal (F0') passes through the UP/DOWN counter 16 and becomes a drive frequency setting signal (Fs). Then, the drive frequency setting signal (Fs) is input to the DDS 17.

The UP/DOWN counter 16 functions during the PLL tracking operation and is used for tracking frequencies. Therefore, the UP/DOWN counter 16 is designed so as to operate only when the input PLL_ON signal is ON. The input PLL_ON signal indicates the end of the detection of the initial resonance frequency (Fro).

The DDS 17 outputs SIN waveforms in accordance with the drive frequency setting signal (Fs), and the SIN waveform output from the DDS 17 is input to the multiplier 15. Then, the output current signal from the CPU 12 is multiplied by the signal DA1, which has been D/A-converted in the D/A converter 14.

The SIN waveforms output from the multiplier 15 are amplified in the power amplifier 19 and are output to the vibrator 2a of the hand piece 2 through the detecting circuit 20.

Here, in the detecting circuit 20, the phase signals of ultrasonic outputs (voltage and current) are θv (voltage phase signal) and θi (current phase signal). The effective value of the output current is |I| and the threshold value |I|ref. The CPU 12 compares the effective value |I| and the threshold value |I| during the detection of the initial resonance frequency (Fro) (during the frequency sweeping). If |I|>|I|ref, the CPU 12 turns on the /PHA_EN, and the /PHA_EN signal is sent to the resonance frequency detecting circuit 21.

The resonance frequency detecting circuit 21 receives the /PHA_EN signal and detects the initial resonance frequency (Fro) based on the switching of the phase difference between θv and θi from + to −. Thus, the shift to the PLL control is achieved, and the PLL_ON signal is turned on.

When the PLL_ON is turned on, the sweep circuit 13 stops the frequency sweeping. Then, changes can be kept below the detected resonance frequency.

Since the PLL_ON is turned on, the operation of the UP/DOWN counter 16 is started. Thus, the resonance frequency tracking by the PLL 41 starts.

Then, the CPU 12 gradually changes the output current signal from 30% to the set value.

The phase comparator 18 detects the phase difference between the voltage phase signal θv and the current phase signal θi and outputs, for the frequency tracking, a control signal (called UP/DOWN signal, hereinafter) for raising or lowering the output frequency of the output (SIN waveform) from the DDS 17. Then, the UP/DOWN signal is input to the UP/DOWN counter 16.

The UP/DOWN counter 16 outputs a drive frequency setting signal (Fs) based on the initial resonance frequency (Fro) detected when the resonance frequency is detected and the UP/DOWN signal from the phase comparator 18. The drive frequency setting signal (Fs) is a frequency setting signal to be actually output from the DDS 17.

In order to detect the initial resonance frequency (Pro) fast once the foot switch 3 is pressed, under the control of the sweeping speed control circuit 24, the D/A converter 23 D/A-converts 3-bits of signals (phase difference amount signal Δθ) representing the amount of the phase difference detected by the phase comparator 18. The output of the D/A converter 23 is output to a VCO 25 so as to become a clock for the sweep circuit 13.

Thus, when the amount of the phase difference between θi and θv is large and when the drive frequency setting signal (Fs) is far from the initial resonance frequency (Fro), the sweeping speed for the detection of the initial resonance frequency (Fro) is increased. When the amount of the phase difference between θi and θv is small, and the drive frequency setting signal (Fs) is near the initial resonance frequency (Fro), the sweeping speed for the detection of the initial resonance frequency (Fro) is decreased.

Therefore, even for the frequency sweeping in a wider range due to the variation of the initial resonance frequencies (Fro) in the production of probes, the sweeping speed is increased with respect to the conventional speed at a point far from the initial resonance frequency (Fro). The conventional sweeping speed is kept at a point near the initial resonance frequency (Fro). Thus, the time until the detection of the initial resonance frequency (Fro) can be reduced securely.

In other words, the speed of frequency sweeping during the detection of the initial resonance frequency (Pro), which is conventionally constant, is increased at a point far from the initial resonance frequency (Pro). The speed of the frequency sweeping is kept in the speed equal to the conventional speed at a point near the initial resonance frequency (Fro). Thus, the Fro detection can be performed securely and faster than the conventional speed.

In the description above, the phase difference amount Δθ is used as a parameter for determining the frequency sweeping speed. However, the effective value |I| of the output current may be detected by a detecting circuit, and the result may be used as the parameter.

Figure 10:
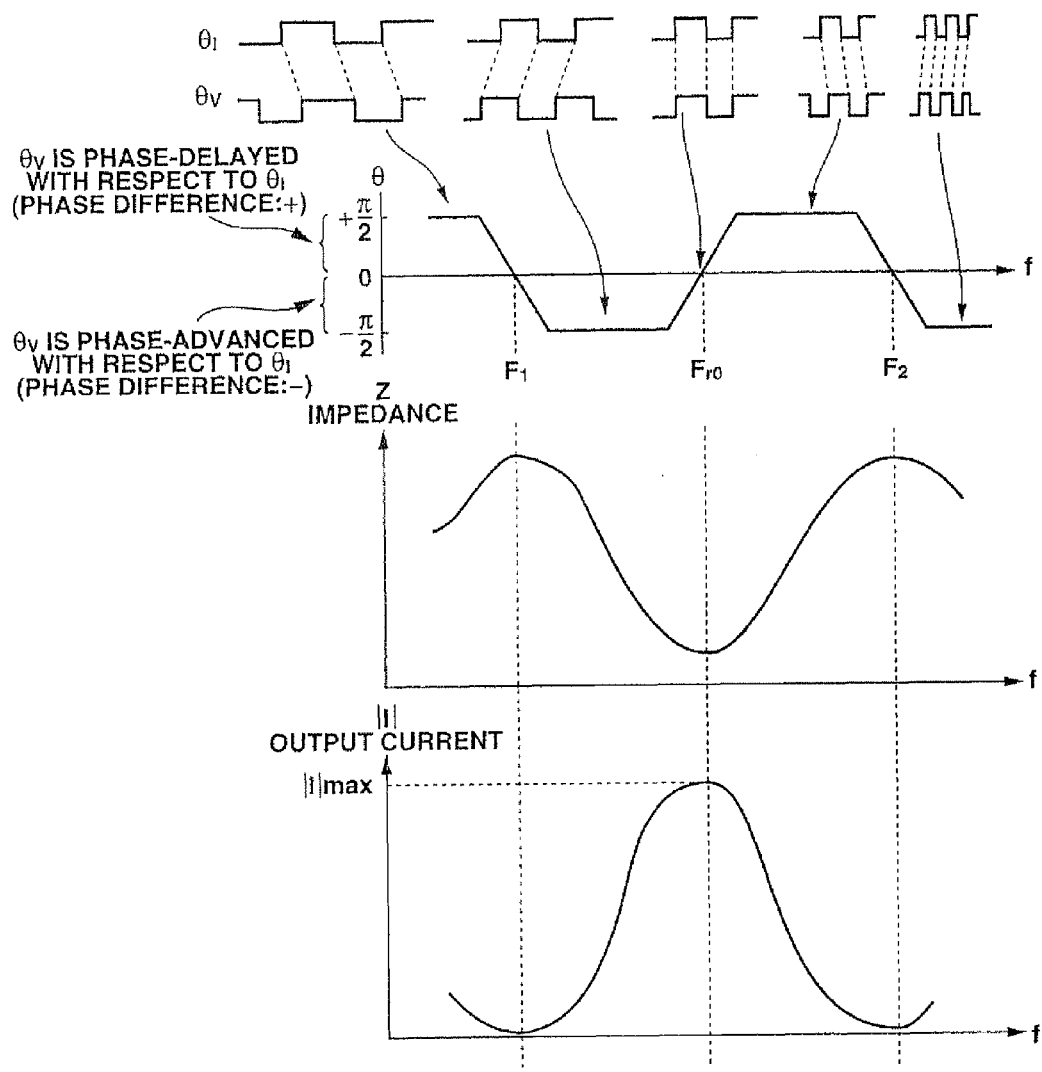
FIGS. 10 to 12 relate to a conventional example.
Figure 11:
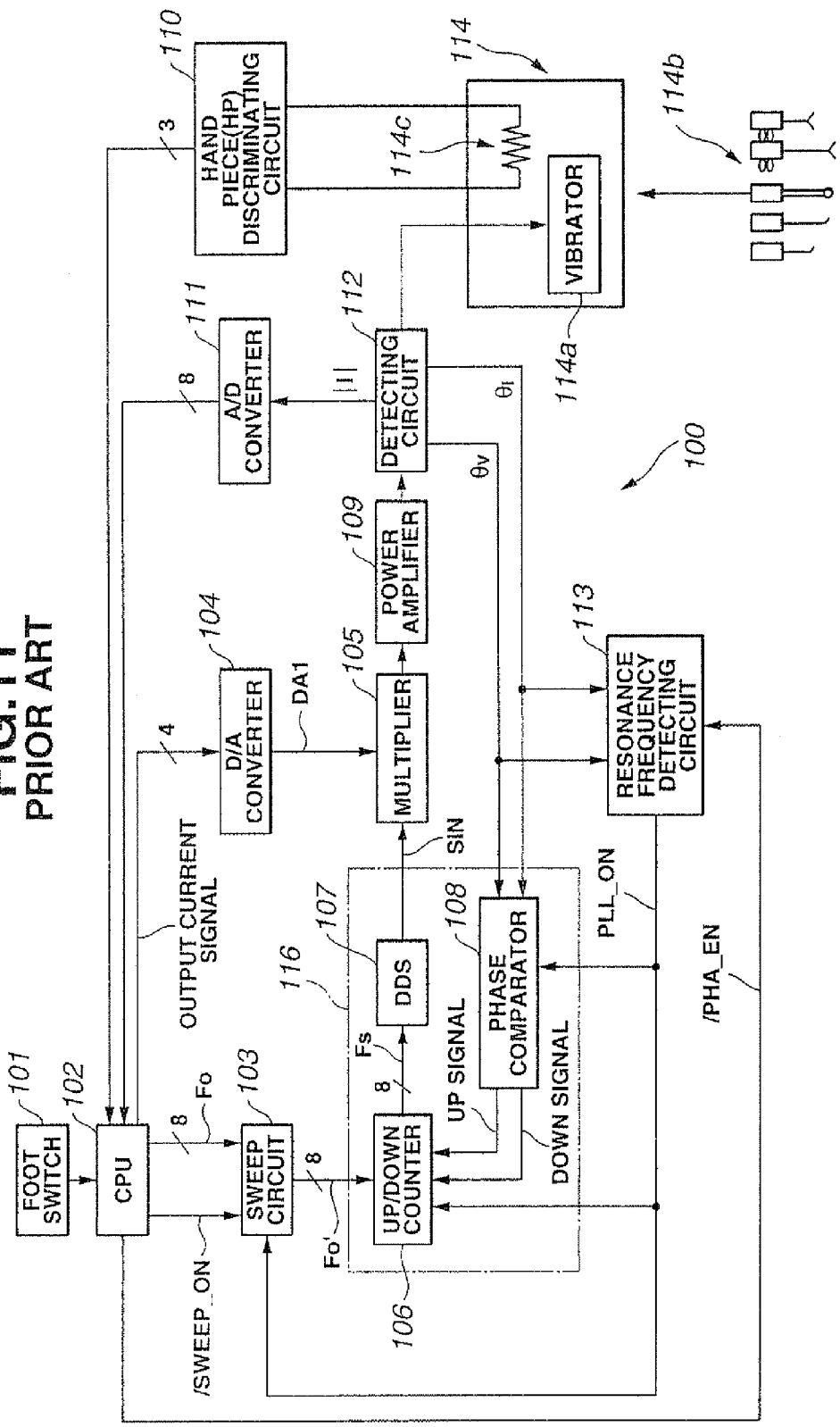
Figure 12:
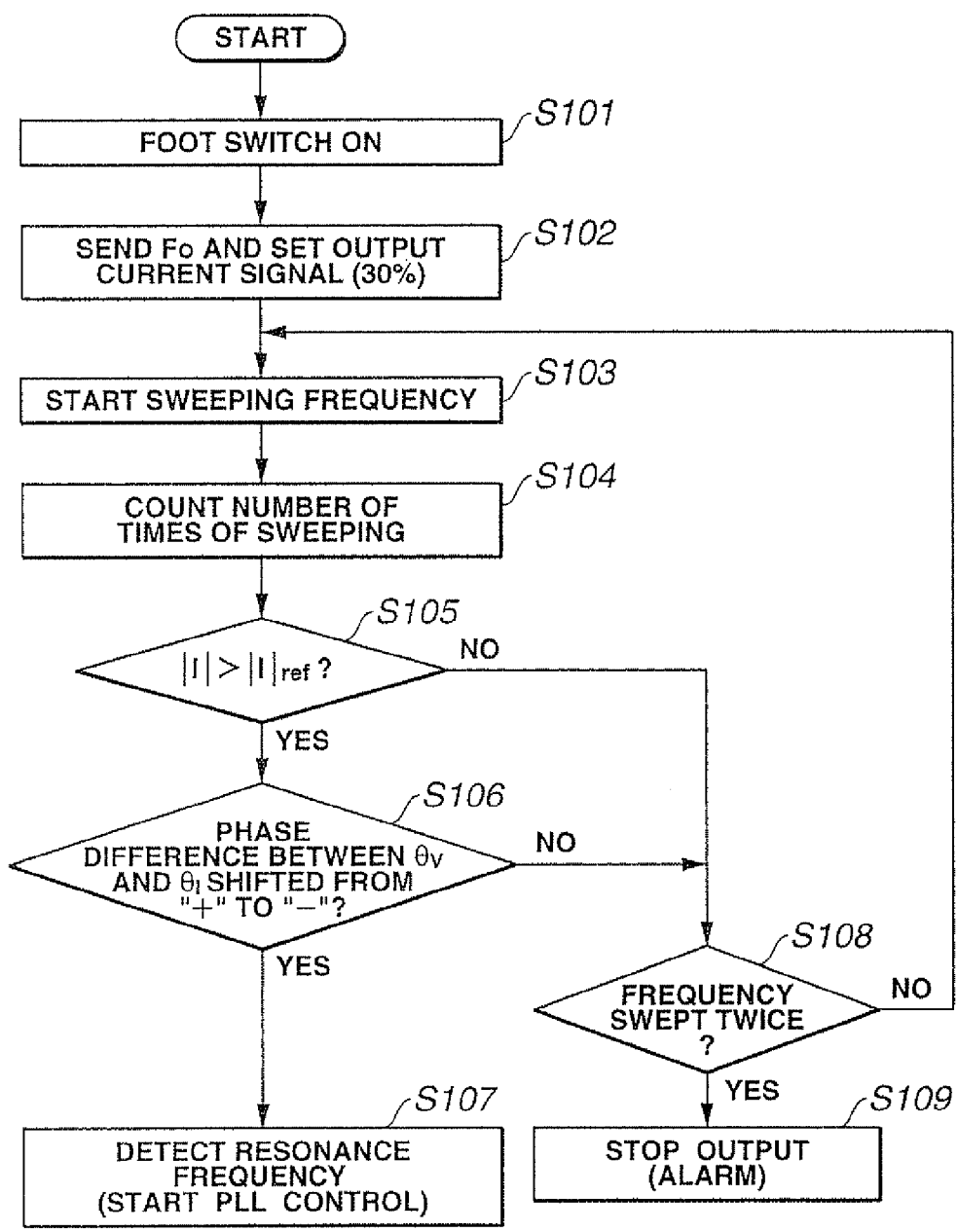

The output voltage decreases near the initial resonance frequency (Fro) and increases with distance from the initial resonance frequency (Fro) (a curb similar to the impedance curb in FIG. 10). Therefore, the output voltage may be used instead of the phase difference amount Δθ in this embodiment.

Figure 3:
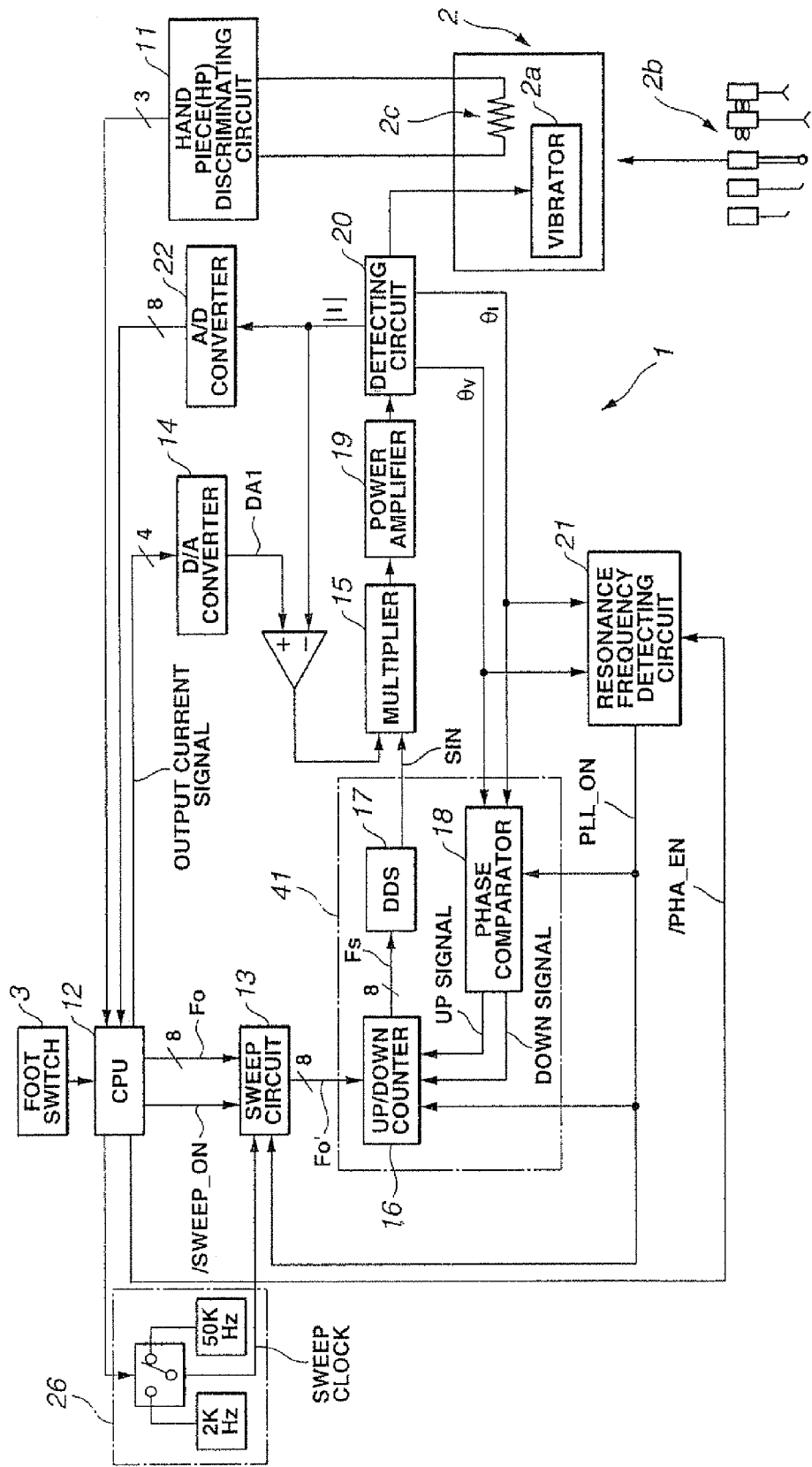

As shown in FIG. 3, the parameter for changing the frequency sweeping speed may be an effective value |I| of the output current. Then, by using the /PHA_EN output from the CPU 12 as a result of the comparison between the effective value |I| and the threshold value |I|ref, the fast frequency and the slow frequency may be switched with a switch for switching the sweeping speed in a swept frequency switching circuit 26. In this case, the same effect as that of the first embodiment can be achieved by adding the minimum circuit construction.

Second Embodiment

A second embodiment is substantially the same as the first embodiment. Therefore, only the differences will be described. The same reference numerals are given to the same components, and the description will be omitted below.

Figure 4:
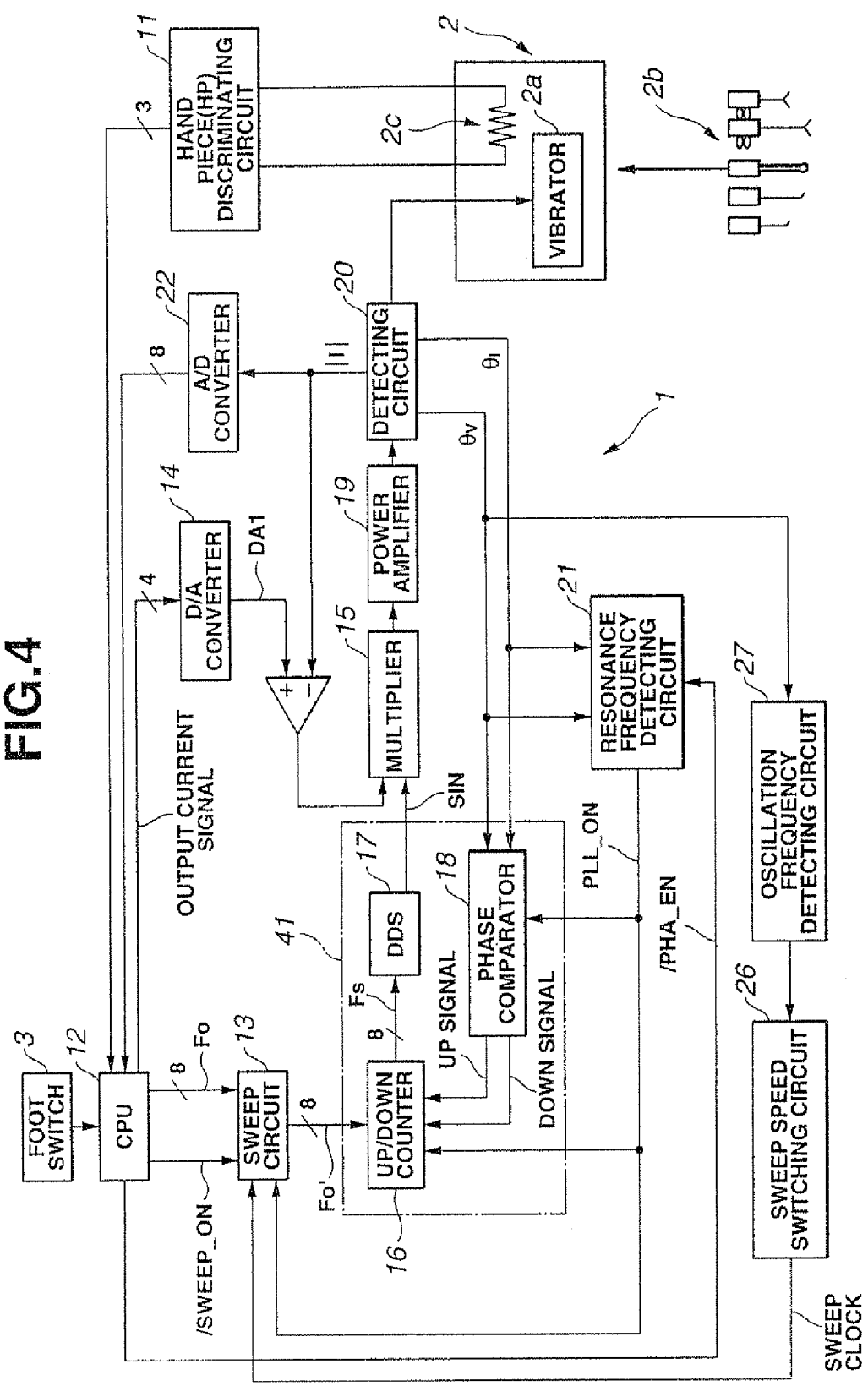
FIGS. 4 and 5 relate to a second embodiment of the present invention.

While the frequency sweeping speed is determined based on the output voltage |V|, output current |I| and phase difference amount Δθ of an ultrasonic output according to the first embodiment, an oscillation frequency detecting circuit 27 detects ultrasonic frequencies generating ultrasonic outputs according to this embodiment, as shown in FIG. 4.

For example, an ultrasonic vibrator having an initial resonance frequency (Fro) close to 20 kHz may be a probe having lower impedance, a large difference between F1 and F2 and easily detectable initial resonance frequency (Fro). An ultrasonic vibrator having an initial resonance frequency (Fro) close to 40 kHz may be a probe having higher impedance, a small difference between F1 and F2 and hard-to-detect initial resonance frequency (Fro). Therefore, when the oscillation frequency detecting circuit 27 detects the output frequency close to 20 kHz, a high frequency is generated from the sweeping speed switching circuit 26. Then, the frequency sweeping is controlled to perform fast. When the oscillation frequency detecting circuit 27 detects the output frequency close to 40 kHz, a low frequency is generated from the sweeping speed switching circuit 26. Then, the frequency sweeping is controlled to perform slowly.

According to this embodiment, the frequency sweeping speed is switched based on the result of the detection of the frequency of θv. However, the same effect can be expected even when the frequency sweeping speed is switched based on the value of the initial resonance frequency (Fro) output from the CPU 12.

In other words, because of the oscillation frequency band, with the oscillation in a frequency band from which the initial resonance frequency (Fro) can be easily detect, the initial resonance frequency (Fro) can be detected faster than the conventional speed by increasing the frequency sweeping speed.

According to the second embodiment, the frequency sweeping speed for the detection of the initial resonance frequency (Fro) is determined based on the difference in oscillation frequency band. However, as shown in FIG. 5, the sweeping speed switching circuit 26 may switch the frequency sweeping speed based on the detection result of the HP discriminating circuit 11.

In this case, a discriminating resistance 2c for hand piece discrimination is set so as to discriminate a probe having a light/heavy impedance, a probe having a small/large difference between F1 and F2 and so on. The probe 2b connectable to the vibrator 2a is determined based on the value of the discriminating resistance 2c. Then, the sweeping speed switching circuit 26 performs the switching.

Therefore, the probe which can easily detect the initial resonance frequency (Fro) and the probe which cannot easily detect the initial resonance frequency can be discriminated based on the discriminating resistance so that the probe, which can easily detect the initial resonance frequency (Fro) can increase the frequency sweeping speed and allows the detection of the initial resonance frequency (Fro) in a shorter period of time than the conventional time.

Figure 5:
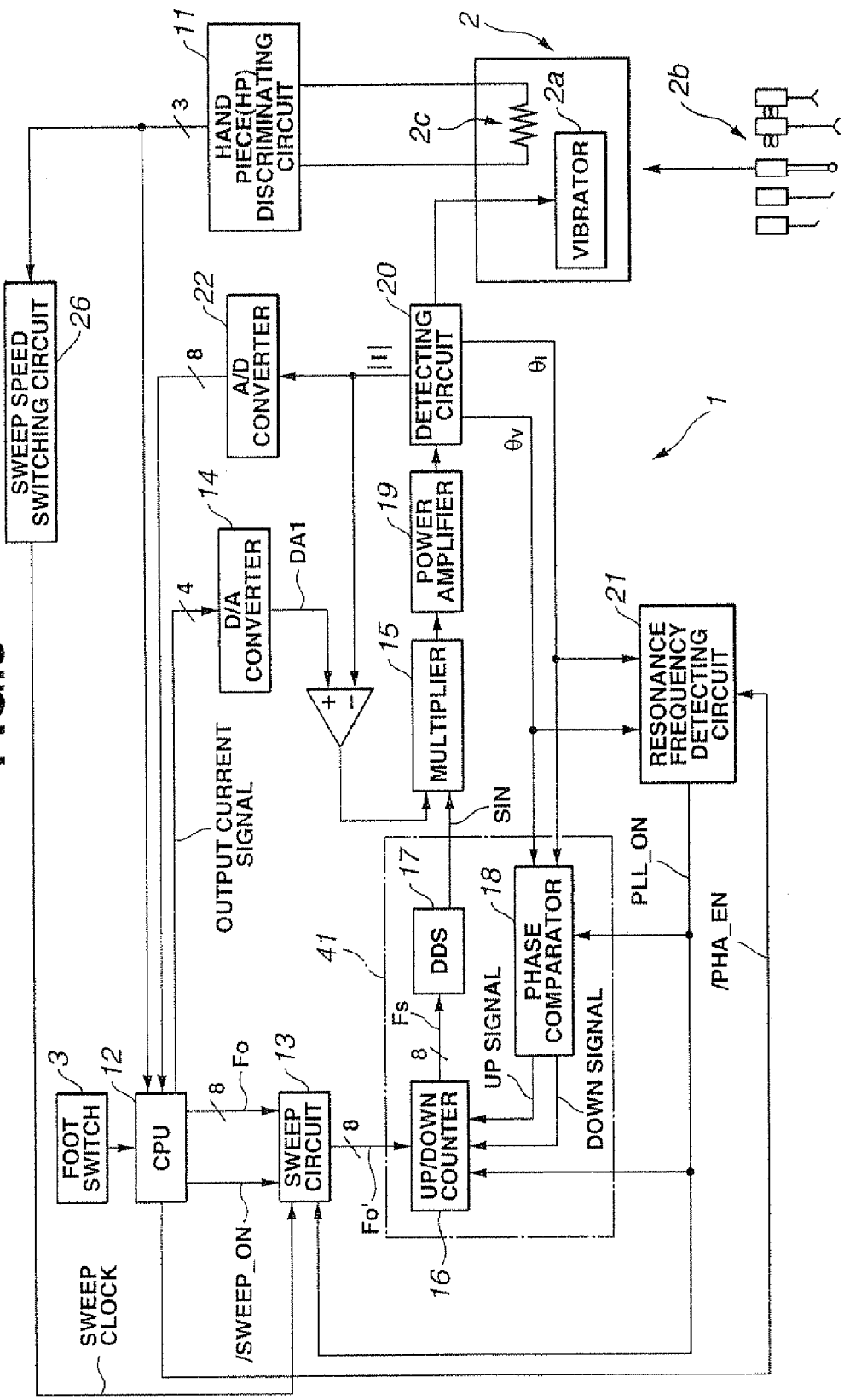

In FIG. 5, the output (HP discriminating signal) of the HP discriminating circuit 11 is directly input to perform the switching. However, the CPU 12 may control based on the input HP discriminating signal and may input a switching signal for the frequency sweeping speed.

Third Embodiment

A third embodiment is substantially the same as the first embodiment. Therefore, only differences will be described. The same reference numerals will be given to the same components, and the description will be omitted.

While the frequency sweeping range is uniquely determined according to the first embodiment, an impedance characteristic of a hand piece 2 is measured before the detection of resonance frequencies according to this embodiment. Then, the frequency sweeping range for the detection of resonance frequencies is determined based on the result.

Figure 6:
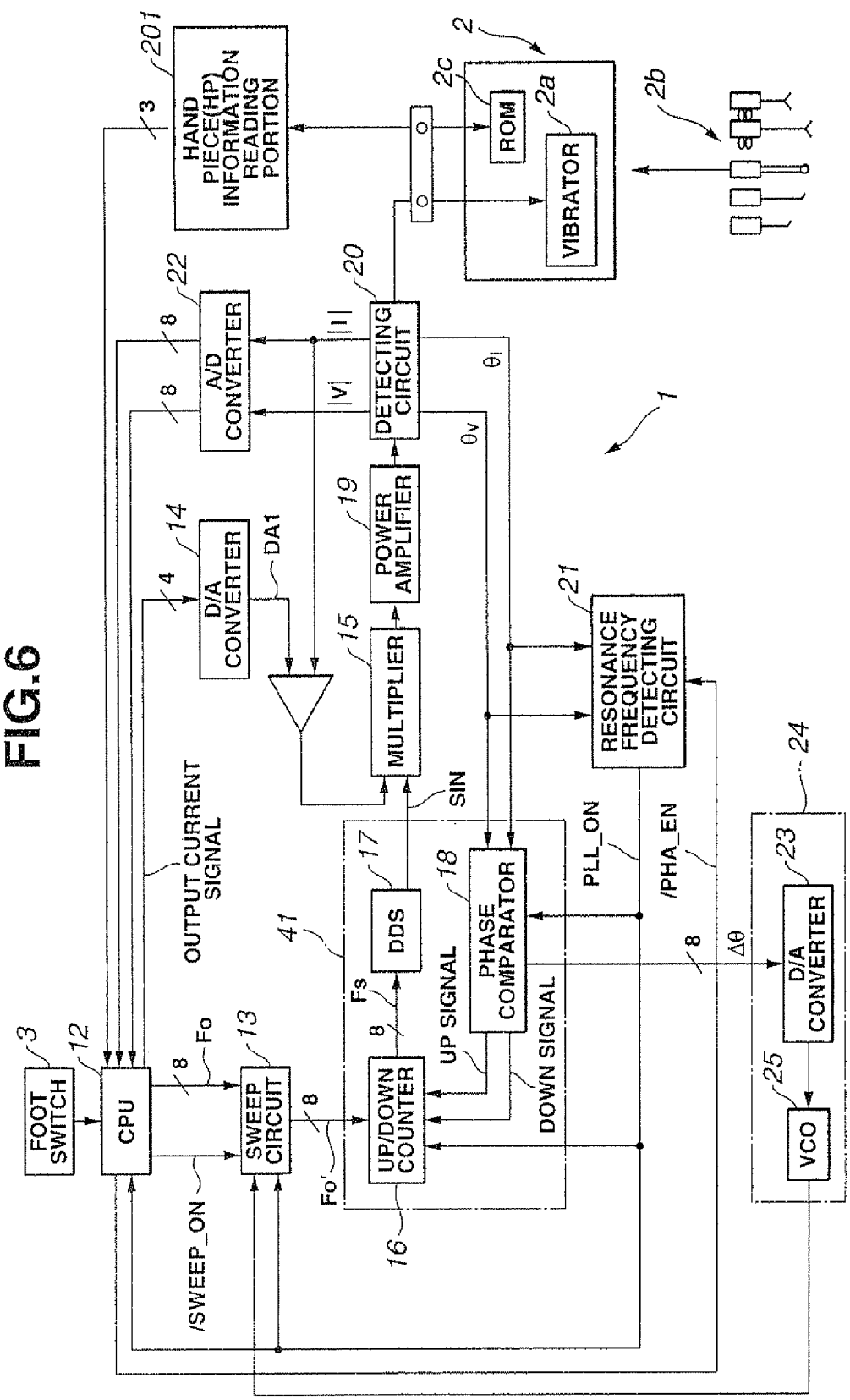
FIG. 6 is a block diagram showing a construction of an ultrasonic operation apparatus according to a third embodiment of the invention.

Therefore, as shown in FIG. 6, the detecting circuit 20 also monitors the effective value |V| of output voltage V. Thus, the CPU 12 can monitor the impedance.

While the discriminating resistance 2c is provided in the hand piece 2 in order to discriminate the type of the hand piece according to the first embodiment. On the other hand, according to this embodiment, a ROM 2c is provided in the hand piece 2. The ROM 2c stores information (such as an ideal resonance frequency, a serial number, a current reference setting value DA1 for the detection of the resonance frequency, a type number, a frequency sweeping speed and error history) relating to the hand piece 2.

The information in the ROM 2c is read by an HP information reading circuit 201. Then, the read data is sent to the CPU 12.

When the hand piece 2 is connected to the ultrasonic coagulation/resection apparatus 1, the HP information reading circuit 201 starts an operation for reading information in the ROM 2c. Then, the read information is sent to the CPU 12.

In response to the information in the ROM 2c, the CPU 12 detects that the hand piece 2 has been connected to the ultrasonic coagulation/resection apparatus 1. Then, in order to check the impedance characteristic, in FIG. 10, of the hand piece 2, the operation by the sweep circuit 13 and the count operation by the UP/DOWN counter 16 are stopped. Then, after the output current is set extremely low, the operation by the sweep circuit 13 is started, and the frequency setting signal for setting the output frequencies are gradually changed through a differential amplifier 202 based on the DA1 and the |I| During these steps, the CPU 12 detects signals from the detecting circuit 20 and the A/D converter 22 to monitor the impedance. Then, the CPU 12 detects the frequency values of the F12 and F2, which are antiresonance frequencies.

When an operator operates the foot switch 3, the CPU 12 sends 8-bits of initial setting frequency signals (F0) to the sweep circuit 13 by avoiding the identified antiresonance frequencies F1 and F2 and performs an operation for detecting resonance frequencies.

The current set value DA1 for the detection of resonance frequencies is changed in accordance with the type of the hand piece 2 or the ROM data in the hand piece 2. Because of the characteristic of the probe, when the hand piece 2 has a large impedance value or is easily under load and the detection of resonance frequencies is difficult to perform, the current set value DA1 is raised. On the other hand, when the hand piece 2 has a small impedance value and the detection of resonance frequencies is easy to perform, the current set value DA1 is lowered.

While the frequency sweep range for the detection of resonance frequencies is uniquely determined in accordance with the type of the hand piece 2 according to the first embodiment, the frequency sweeping range can be set in accordance with the hand piece 2 according to this embodiment. Thus, resonance frequencies can be detected without the misdetection of the antiresonance frequencies F1 and F2 of the hand piece 2 as the resonance frequency Fro during the detection of the resonance frequencies after the manipulation of the foot switch 3.

By changing the current setting for the detection of resonance frequencies in accordance with the type of the hand piece 2 or the ROM data in the hand piece 2, the resonance frequencies can be detected efficiently.

According to this embodiment, the antiresonance frequencies F1 and F2 due to the impedance are detected when the hand piece 2 is connected. However, a specific switch different from the foot switch 3 may be provided. When an operator manipulates the specific switch, the impedance characteristic can be checked. When the impedance characteristic has a small variation and has a tendency in characteristic, the ROM in the hand piece 2 may store the frequency sweeping range.

In order to set the current for the detection of resonance frequencies, the magnitude of the impedance may be measured for checking the impedance characteristic. The current for the detection of the resonance frequencies can be set in accordance with the measured magnitude.

Fourth Embodiment

A fourth embodiment is substantially the same as the third embodiment. Therefore, only the differences will be described. The same reference numerals will be given to the same components, and the description will be omitted.

Figure 7:
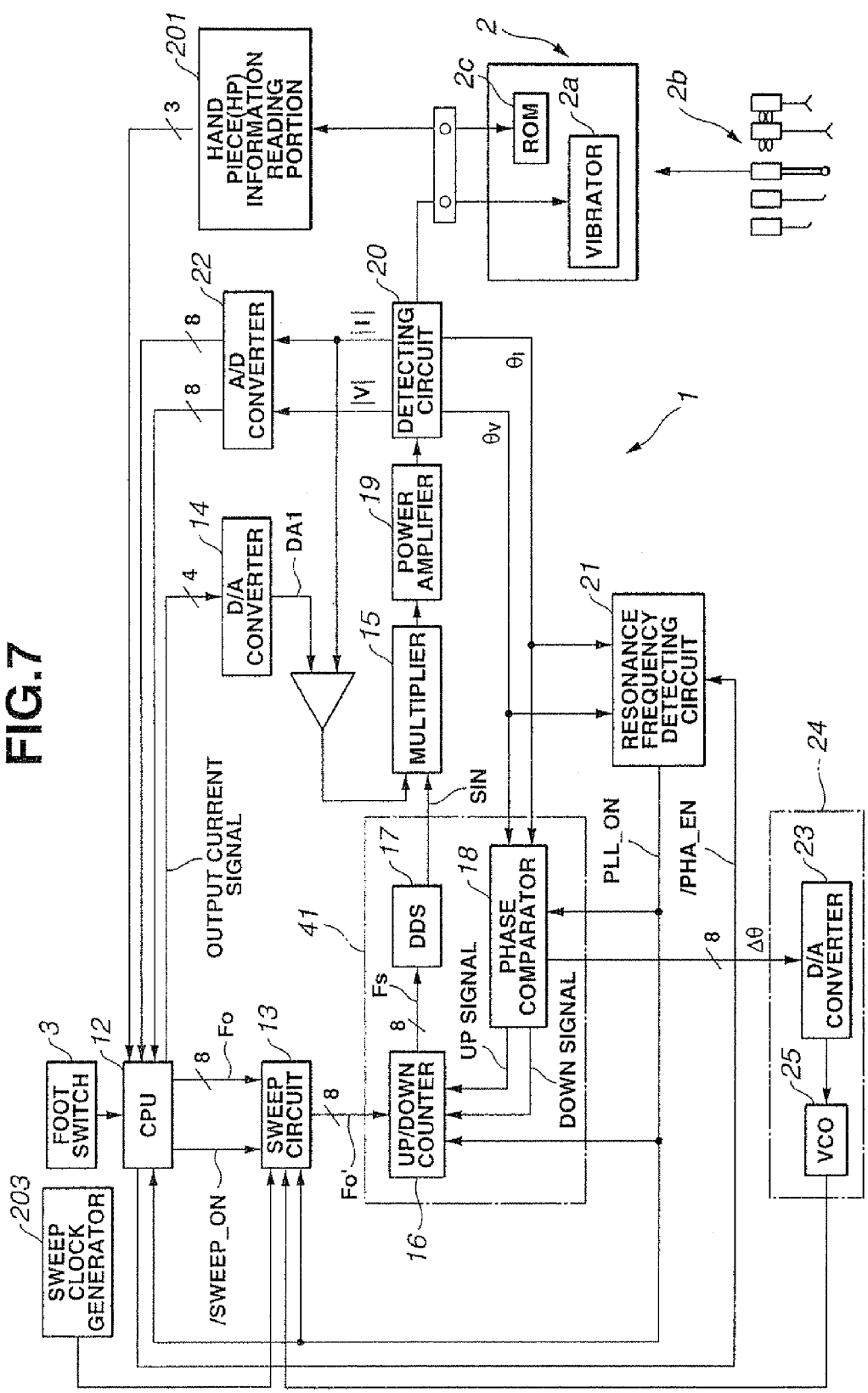
FIG. 7 is a block diagram showing a construction of an ultrasonic operation apparatus according to a fourth embodiment of the invention.

While the frequency sweeping speed is changed by detecting the phase difference amount $\Delta\theta$, inputting the magnitude to the VCO 25 and changing the clock speed of the sweep circuit 13 according to the third embodiment, a sweep clock generating circuit 203 is provided so as to keep clocks constant, as shown in FIG. 7, according to the fourth embodiment. However, a phase difference amount $\Delta\theta$ is input to the sweep circuit 13. When the phase difference amount $\Delta\theta$ is large, the step of the sweep frequency for the detection of resonance frequencies is increased (such as an increase by 10 Hz). When the phase difference amount $\Delta\theta$ is small, the step of the sweep frequency for the detection of resonance frequencies is decreased (such as a decrease by 1 Hz).

As described above, the same effect can be obtained as that of the third embodiment without changes in clock for frequency sweeping.

Fifth Embodiment

A fifth embodiment is substantially the same as the third embodiment. Therefore, only differences will be described. The same reference numerals will be given to the same components, and the description will be omitted below.

Figure 8:
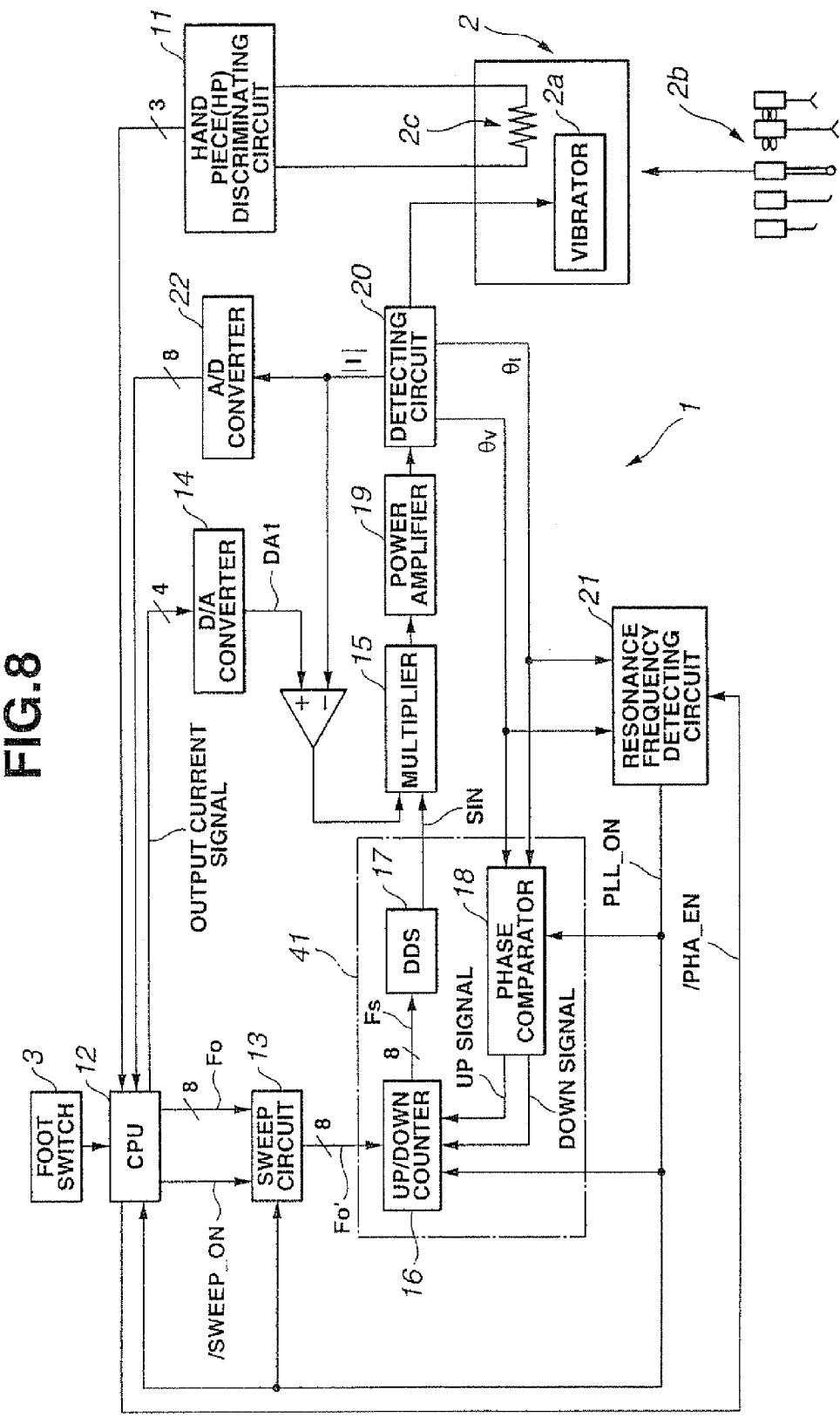
FIGS. 8 and 9 relate to a fifth embodiment of the invention.

According to the third embodiment, the ROM 2c is provided in the hand piece 2, and the ROM 2c stores the current set value for the detection of resonance frequencies. Thus, the current set value for the detection of resonance frequencies can be changed by the hand piece 2. On the other hand, according to the fifth embodiment, as shown in FIG. 8, a resistance 2c cheaper than a ROM is provided in the hand piece 2. The HP discriminating circuit 11 includes a transformer, and power is supplied to the resistance 2c through the transformer. The voltage value of the primary side of the transformer is measured, and the impedance is detected. Based on the value, the type of the hand piece is discriminated.

The result from the discrimination of the type of the hand piece is sent to the CPU 12, and the CPU 12 sets the current set value DA1 and frequency range for the detection of the resonance frequencies.

For example, when the hand piece 2 has a high impedance characteristic, the current setting for the resonance frequency detection is raised. On the other hand, when the hand piece 2 has a low impedance characteristic, the current setting for resonance frequencies is lowered.

The hand piece discriminating circuit 11 detects the impedance value of the resistance 2c and sends digital signals in accordance with the type of the hand piece 2 to the CPU 12. Alternatively, the CPU 12 may read the voltage value through the A/D 22 converter to detect the impedance value.

Figure 9:
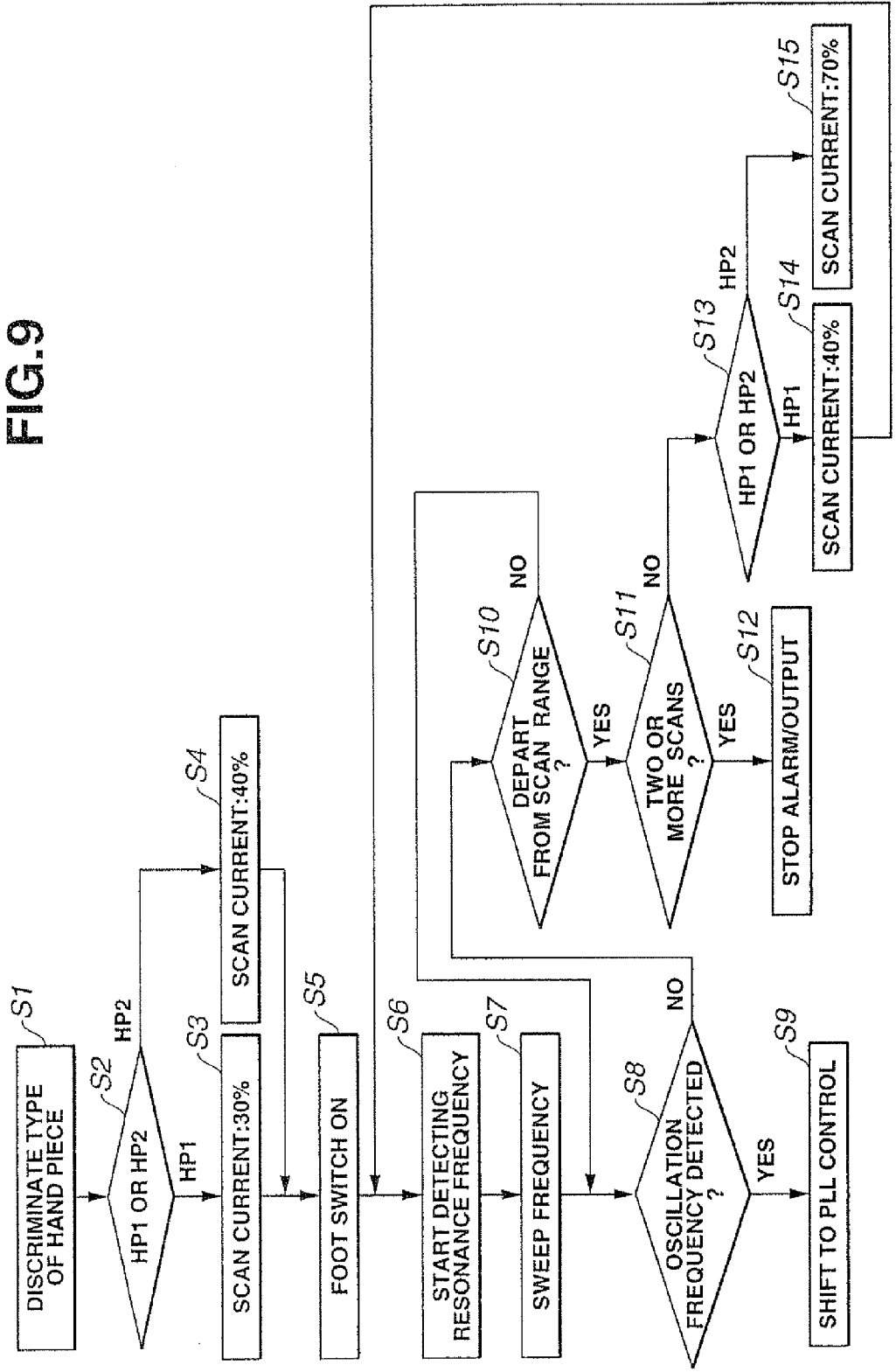

FIG. 9 shows a control flow according to this embodiment. As shown in FIG. 9, the HP detection is performed at a step S1 to detect the type of the hand piece 2 connected to the apparatus.

At a step S2, the detection result of the type of the hand piece 2 at the step S1 is received, and whether the hand piece (HP) 1 or hand piece (HP) 2 is connected to the apparatus is determined. At steps S3 and S4, the current value for the resonance frequency detection is set.

When HP 1 is connected to the apparatus, the current set value for the resonance frequency detection is 30% at the step S3. When the HP 2 is connected, the current set value for the resonance frequency detection is 50% at the step S4.

At a step S5, an operator turns on the foot switch 3. Then, at a step S6, the resonance frequency detection is started (that is, the control signal for the resonance frequency detection is turned on, and a start frequency signal for frequency sweeping and the current set value are sent).

Then, at a step S7, the frequency sweeping is performed. At a step S8, when a resonance frequency is detected during the frequency sweeping for the resonance frequency detection, the processing shifts to PLL control at a step S9.

In order to shift to PLL control at the step S9, a signal indicating that a resonance frequency could be detected is sent to the CPU 12, the sweep circuit 13 and the UP/DOWN counter 16. Then, the sweep circuit 13 stops the frequency sweeping operation. The UP/DOWN counter 16 receives the output from the phase comparator 18, and the UP/DOWN counting of output frequencies is performed. Thus, the shift to PLL control is allowed.

When a resonance frequency cannot be detected at the step S8, whether the sweeping departs from the frequency sweeping range for resonance frequency detection or not is determined at a step S10. If not, the processing returns to the step S7. If so, the number of times of resonance frequency detentions is determined at a step S11.

When it is determined at a step S11 that the number of times of resonance frequency detection is two, no more resonance frequency detection is performed. Then, the output is terminated and an alarm is given at a step S12. If it is determined at the step S11 that the number of times of the resonance frequency detection is one, the type of the HP is determined at a step S13.

If the hand piece is the HP 1, the resonance frequency detecting current is 40% (+10% for the first resonance frequency detection) at a step S14 and then returns to the step S6. If the hand piece is the HP 2, the resonance frequency detecting current is 70% (+20% for the second resonance frequency detection) at a step S15. Then, the processing returns to the step S6.

By returning to the step S6, the second resonance frequency detection is performed after the setting of the current for the resonance frequency detection is changed at the steps S14 and 15.

According to this embodiment, the current set value for the resonance frequency detection is changed in accordance with the type of the hand piece.

For the hand piece having high impedance, the current set value for the resonance frequency detection is increased. Thus, the output voltage is increased, and the resonance frequencies can be detected more easily.

The amount of change from the current setting for the first resonance frequency detection to the current setting for the second resonance frequency detection may be changed in accordance with the type of the hand piece. Thus, the resonance frequency detection is controlled to be more reliable.

It is apparent that various embodiments of the present invention are possible based on this specification without departing from the spirit and scope of the invention. The present invention is only limited by the appended claims and is not limited by any specific embodiments.

What is claimed is:

1. An ultrasonic operation apparatus, comprising:
a hand piece having an ultrasonic vibrator configured to cause ultrasonic vibrations, and a probe configured to treat by transmitting the ultrasonic vibrations from the ultrasonic vibrator to a living body tissue;
a driver, removably connected to the hand piece, having a driving signal generating portion configured to generate a driving signal for driving the ultrasonic vibrator;
a discriminating portion configured to discriminate the hand piece connected to the driver;
a sweep portion configured to sweep the driving signal supplied from the driving signal generating portion to the ultrasonic vibrator based on a discrimination result of the discriminating portion;
a sweeping speed control portion configured to control a sweeping speed of the sweep portion based on a condition information of the driving signal swept by the sweep portion;
a resonance point detecting portion configured to detect a resonance point of the ultrasonic vibrator of the hand piece from a driving signal having a sweeping speed changed by the sweeping speed control portion; and
a tracking and control portion configured to track and control the resonance point based on a detection result of the resonance point detecting portion and a phase information of the driving signal.

2. An ultrasonic operation apparatus according to claim 1, wherein the sweeping speed control portion controls the sweeping speed based on a difference amount between a voltage phase and a current phase of the swept driving signal.

3. An ultrasonic operation apparatus according to claim 1, wherein the sweeping speed control portion controls the sweeping speed based on a current effective value of the swept driving signal.

4. An ultrasonic operation apparatus according to claim 1, wherein the sweeping speed control portion controls the sweeping speed based on a frequency band of the swept driving signal.

5. An ultrasonic operation apparatus, comprising:
a removable hand piece, having an ultrasonic vibrator configured to cause ultrasonic vibrations, and a probe configured to transmit the ultrasonic vibrations from the ultrasonic vibrator;
a driving signal generating portion for generating a driving signal, which drives the ultrasonic vibrator;
a tracking and control portion configured to track and control a resonance point of the ultrasonic vibrator based on a phase information of the driving signal supplied from the driving signal generating portion to the ultrasonic vibrator;
a sweep portion configured to sweep the driving signal;
a sweeping speed control portion configured to control a sweeping speed of the sweep portion; and
an operation control portion configured to control an operation of the tracking and control portion by detecting a resonance point of the ultrasonic vibrator from a driving signal swept by the sweep portion, the sweeping speed of which is controlled by the sweeping speed control portion.

6. An ultrasonic operation apparatus according to claim 5, wherein the sweeping speed control portion controls the sweeping speed based on a difference amount between a voltage phase and a current phase of the swept driving signal.

7. An ultrasonic operation apparatus according to claim 5, wherein the sweeping speed control portion controls the sweeping speed based on a current effective value of the swept driving signal.

8. An ultrasonic operation apparatus according to claim 5, wherein the sweeping speed control portion controls the sweeping speed based on a frequency band of the swept driving signal.

9. An ultrasonic driving apparatus, comprising:
a driving signal generating portion configured to generate a driving signal, which drives an ultrasonic vibrator;
a sweep portion configured to sweep the driving signal supplied from the driving signal generating portion to the ultrasonic vibrator;
a sweeping speed control portion configured to control a sweeping speed of the sweep portion;
a resonance point detecting portion configured to detect a resonance point of the ultrasonic vibrator based on the driving signal swept by the sweep portion, the sweeping speed of which is controlled by the sweeping speed control portion; and
a tracking and control portion configured to track and control the resonance point of the ultrasonic vibrator based on a detection result by the resonance point detecting portion and a phase information of the driving signal.

10. An ultrasonic driving apparatus according to claim 9, wherein the sweeping speed control portion controls the sweeping speed based on a difference amount between a voltage phase and a current phase of the swept driving signal.

11. An ultrasonic driving apparatus according to claim 9, wherein the sweeping speed control portion controls the sweeping speed based on a current effective value of the swept driving signal.

12. An ultrasonic driving apparatus according to claim 9, wherein the sweeping speed control portion controls the sweeping speed based on a frequency band of the swept driving signal.

13. An ultrasonic driving apparatus, comprising:
a driving signal generating portion configured to generate a driving signal, which drives an ultrasonic vibrator;
an impedance detecting portion configured to detect an impedance of the ultrasonic vibrator based on the driving signal supplied from the driving signal generating portion to the ultrasonic vibrator;
a sweep portion configured to sweep the driving signal;
a sweep range setting portion configured to set a sweep range of the sweep portion based on a detection result by the impedance detecting portion;
a sweeping speed control portion configured to control a sweeping speed of the sweep portion;
a resonance point detecting portion configured to detect a resonance point of the ultrasonic vibrator based on the driving signal swept by the sweep portion under the control of the sweeping speed control portion and the sweep range setting portion; and
a tracking and control portion configured to track and control the resonance point of the ultrasonic vibrator based on a detection result by the resonance point detecting portion and a phase information of the driving signal.

14. An ultrasonic driving apparatus, comprising:
a removable hand piece having an ultrasonic vibrator configured to cause ultrasonic vibrations, and a probe configured to transmit the ultrasonic vibrations from the ultrasonic vibrator;
driving signal generating means for generating a driving signal, which drives the ultrasonic vibrator;
tracking and control means for tracking and controlling a resonance point of the ultrasonic vibrator based on a phase information of the driving signal supplied from the driving signal generating means to the ultrasonic vibrator;
sweep means for sweeping the driving signal;
sweeping speed control means for controlling a sweeping speed of the sweep means; and
operation control means for controlling an operation of the tracking and control means by detecting a resonance point of the ultrasonic vibrator from a driving signal swept by the sweep means, the sweeping speed of which is controlled by the sweeping speed control means.

15. An ultrasonic driving apparatus, comprising:
driving signal generating means for generating a driving signal, which drives an ultrasonic vibrator;
sweep means for sweeping the driving signal supplied from the driving signal generating means to the ultrasonic vibrator;
sweeping speed control means for controlling a sweeping speed of the sweep means;
resonance point detecting means for detecting a resonance point of the ultrasonic vibrator based on a driving signal swept by the sweep means, the sweeping speed of which is controlled by the sweeping speed control means; and
tracking and control means for tracking and controlling the resonance point of the ultrasonic vibrator based on a detection result by the resonance point detecting means and the phase information of the driving signal.

16. An ultrasonic driving apparatus, comprising:
driving signal generating means for generating a driving signal, which drives an ultrasonic vibrator;
impedance detecting means for detecting an impedance of the ultrasonic vibrator based on the driving signal supplied from the driving signal generating means to the ultrasonic vibrator;
sweep means for sweeping the driving signal;
sweep range setting means for setting a sweep range of the sweep means based on the detection result by the impedance detecting means;
sweeping speed control means for controlling a sweeping speed of the sweep means;
resonance point detecting means for detecting a resonance point of the ultrasonic vibrator based on the driving signal swept by the sweep means under the control of the sweeping speed control means and the sweep range setting means; and
tracking and control means for tracking and controlling the resonance point of the ultrasonic vibrator based on a detection result by the resonance point detecting means and the phase information of the driving signal.

* * * * *